US00PP31604P2

(12) United States Plant Patent
Olesen

(10) Patent No.: US PP31,604 P2
(45) Date of Patent: Mar. 31, 2020

(54) COMPACT FLORIBUNDA ROSE PLANT NAMED 'POULPAL069'

(50) Latin Name: ***Rosa* hybrid**
Varietal Denomination: Poulpal069

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,575

(22) Filed: Sep. 4, 2018

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./145
See application file for complete search history.

(56) References Cited

PUBLICATIONS

Perfection by Poulsen Novelties 2013/2014, www.poulsenroser.dk/media/116439/Introductions-seg-3-4_2013-2014_GBP.pdf, p. 3 under "Palace", downloaded from the web on Jun. 6, 2019.*
UPOV hit on a floribunda rose named 'Poulpal069', QZ PBR 20172255, filed Sep. 19, 2017.*

* cited by examiner

*Primary Examiner* — Anne Marie Grunberg

(57) ABSTRACT

A new garden rose plant of the Compact Floribunda class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal069'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpal069', originated as a single seedling from the stated cross.

The new variety may be distinguished from its male pollen parent and female seed parent primarily by the following characteristics. The male pollen parent plant has red orange blend flowers while the new variety has yellow flowers. The female seed parent plant has apricot flowers while the new variety has yellow flowers.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpal069' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpal069' was selected in the spring of 2008 by the inventor as a single plant from the progeny of the aforementioned hybridization.

Asexual reproduction of 'Poulpal069' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpal069' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal069'. Specifically illustrated in the drawing are a cluster of open flowers on a branch, a flower bud after opening, open flower viewed from above, flower petals detached, sepals detached showing reproductive flower parts, and a leaf. Plants shown are 2 years of age.

DETAILED DESCRIPTION OF THE VARIETY

The following is a description of 'Poulpal069', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpal056', U.S. Plant Pat. No. 26,536 are compared to 'Poulpal069' in Chart 1.

CHART 1

| | 'Poulpal069' | 'Poulpal056' |
|---|---|---|
| Petal Count | 30 | 50 |
| Flower Diameter | 70 mm | 50-60 mm |
| General Tonality of Flower Color | Yellow Group 12A | Yellow Group 12A |

FLOWER AND FLOWER BUD

Blooming habit: Continuous.

Flower bud:

*Size.*—Upon opening, 25 mm in length from base of receptacle to end of bud. Bud diameter is 15 mm.

*Bud form.*—Ovoid, with a broad base.

*Bud color.*—As sepals divide petals are Yellow Group 12A and Orange-Red Group N34A.

*Sepal inner surface.*—Color: Yellow-Green Group 147C. Surface: Lightly pubescent.

*Sepal outer surface.*—Color: Yellow-Green Group 144A with very strong intonations of Greyed-Purple Group 187A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—20 mm long, 7 mm wide.

*Receptacle.*—Texture: Smooth. Size: 9 mm in height, 8 mm wide. Color: Yellow-Green Group 144A. Shape: Globular.

*Pedicel.*—Surface: Smooth. Length: 25 mm. Diameter: 2 mm on average. Color: Yellow-Green Group N144A, with intonations of Greyed-Purple Group 184B. Strength: Strong.

*Peduncle.*—Length: About 20 cm. Diameter: About 4 mm. Color: Greyed-Red Group 181A and Yellow-Green Group 144A. Texture: Smooth.

Flower bud development: Flower buds are borne in clusters of 3 to 5 flower buds per stem.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 70 mm when open. Flower depth is 35 mm.

*Flower shape.*—Open cup, double flower, with petals that curve out from the center.

*Shape of flower, side view.*—The upper portion is a flattened convex. The lower portion is concave.

Petalage: Under normal conditions, flowers have about 30 petals.

General tonality of flower: Open flowers are Yellow Group 12A.

Petal color:

*Upon opening, outer and inner petals.*—Upper surface: Yellow Group 12A. Lower surface: Yellow Group 13C. No distinctive coloration at the petal base observed.

*After opening, outer and inner petals.*—Upper surface: Yellow Group 9B. Yellow Group 10B, at basal section. Lower surface: Yellow Group 10A.

Petals:

*Petal reflex.*—Outer petals reflex slightly. Inner petals do not reflex.

*Margin.*—Entire and uniform, with occasional clefts. Moderate to strong undulations.

*Shape.*—Broad and elliptic.

*Apex shape.*—Rounded.

*Base shape.*—Broadly acute.

*Size.*—35 mm (l)×36 mm (w).

*Texture.*—Smooth.

*Thickness.*—Average.

Petaloids:

*Size.*—25 mm (l) by 15 mm (w).

*Quantity.*—About 10.

*Shape.*—Elliptical with an acute base and rounded apices.

*Color.*—Upper surface Yellow Group 12A. Lower surface Yellow Group 13C.

Reproductive flower parts:

*Pollen.*—None observed.

*Anthers.*—Size: 3 mm in length. Color: Yellow Group 6B. Quantity: 35 on average.

*Filaments.*—Color: Yellow-Orange Group 23A, Length: 5 mm.

*Pistils.*—Length: 6 mm. Quantity: 25 on average.

*Stigmas.*—Color: Green-White Group 157A.

*Styles.*—Color: Green-White Group 157A.

*Location of stigmas.*—Inferior in location relative to the length of the filaments and the height of the anthers.

*Hips.*—None Observed.

PLANT

Plant growth: Upright, bushy. Plants are 40 cm in height, and 30 cm wide.

Stems:

*Color of juvenile growth.*—Yellow-Green Group 144B, with intonations of Greyed-Purple Group 185A.

*Color of mature growth.*—Yellow-Green Group 146A.

*Length.*—Canes are about 20 cm from the base of the plant to the flowering portion.

*Diameter.*—About 9 mm.

*Internodes.*—On mature canes about 45 mm between nodes.

*Surface texture.*—Young wood: Smooth. Older wood: Smooth.

Long prickles:

*Incidence.*—About 7 prickles per 10 cm of stem.

*Size.*—Average length of prickles on mature stems is 9 mm.

*Shape.*—Upper portion is linear. Lower portion is concave.

*Color.*—Juvenile prickles: Greyed-Red Group 181A. Mature prickles: Greyed-Red Group 181A.

Plant foliage:

*Compound leaf.*—130 mm (l)×95 (w).

*Quantity.*—2 leaves per 10 cm of stem on average.

*Leaf bearing angle to the stem.*—45 degrees.

*Color of juvenile foliage*.—Upper side: Yellow-Green Group 144A. Lower side: Yellow-Green Group 144B.

*Color of mature foliage*.—Upper side: Yellow-Green Group 146B. Lower side: Yellow-Green Group 146C.

Plant leaves and leaflets:

*Stipules*.—Size: 20 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 2 mm. Upper surface color: Yellow-Green Group 144A with intonations of Greyed-Purple Group 185A. Lower surface color: Yellow-Green Group 144A.

*Rachis*.—Length: 40 mm. Upper surface color: Yellow-Green Group 144A with intonations of Greyed-Purple Group 185A. Lower surface color: Yellow-Green Group 144A.

*Leaflet*.—Quantity: Normally 5 leaflets. Margins: Serrated. Size: Terminal leaflets are about 55 mm long, 35 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the compact floribunda rose class named 'Poulpal069', substantially as illustrated and described herein, due to its abundant yellow flowers, disease resistance, and extended period of bloom.

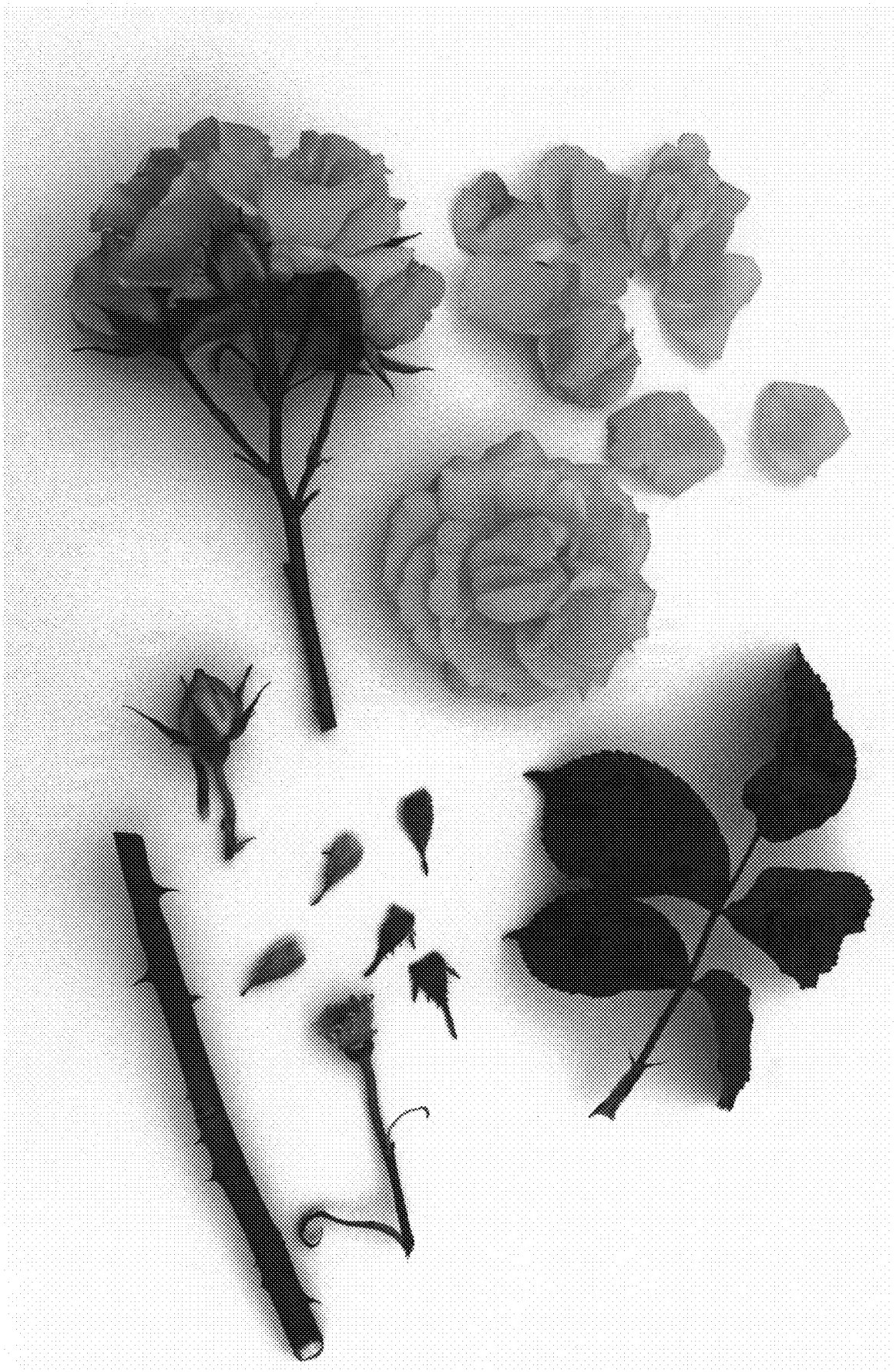

* * * * *